(12) United States Patent
Greaves

(10) Patent No.: US 9,533,171 B2
(45) Date of Patent: Jan. 3, 2017

(54) METHOD FOR TREATING ACNE

(71) Applicant: L'OREAL, Paris (FR)

(72) Inventor: Andrew Greaves, Magny-le-Hongre (FR)

(73) Assignee: L'OREAL, Paris (FR)

(*) Notice: Subject to any disclaimer, the term of this patent is extended or adjusted under 35 U.S.C. 154(b) by 424 days.

(21) Appl. No.: 13/915,940

(22) Filed: Jun. 12, 2013

(65) Prior Publication Data

US 2014/0024996 A1 Jan. 23, 2014

Related U.S. Application Data

(60) Provisional application No. 61/660,171, filed on Jun. 15, 2012.

(51) Int. Cl.
*A61N 5/06* (2006.01)

(52) U.S. Cl.
CPC ........... *A61N 5/0624* (2013.01); *A61N 5/0616* (2013.01); *A61N 2005/0662* (2013.01)

(58) Field of Classification Search
CPC .... A61N 5/0616; A61N 5/062; A61N 5/0624; A61N 2005/0661; A61N 2005/0662
USPC ......................................... 606/9; 607/88, 89
See application file for complete search history.

(56) References Cited

U.S. PATENT DOCUMENTS

| | | | | |
|---|---|---|---|---|
| 4,495,079 A | * | 1/1985 | Good | 510/137 |
| 5,366,665 A | * | 11/1994 | Cho | 510/152 |
| 5,769,844 A | * | 6/1998 | Ghaffari | A61B 18/22 |
| | | | | 362/298 |
| 2003/0185915 A1 | * | 10/2003 | Carlo et al. | 424/744 |
| 2010/0196343 A1 | * | 8/2010 | O'Neil | A61B 18/203 |
| | | | | 424/94.4 |
| 2010/0267598 A1 | * | 10/2010 | Sans | A61K 8/345 |
| | | | | 510/130 |

FOREIGN PATENT DOCUMENTS

WO WO-2009077960 A1 6/2009

OTHER PUBLICATIONS

The internet webpage http://lightstim.com/how-to-use-the-led-photo-rejuvenation-lights.html archived on Aug. 16, 2009 (retrieved on Jul. 16, 2015), backdated using the Internet Archive Wayback Machine.*
XP-002670946 LightStim—How to use the LightStim, Oct. 28, 2010.

* cited by examiner

*Primary Examiner* — Lynsey Crandall
*Assistant Examiner* — Nathan J Jenness
(74) *Attorney, Agent, or Firm* — Polsinelli PC

(57) ABSTRACT

The invention relates to a method for preventing and/or treating skin disorders related to *Propionibacterium acnes*, comprising a step consisting in applying, to acneic skin, a dermatological composition comprising, in a physiologically acceptable medium, at least one anionic surfactant in an amount ranging from 0.001% to 0.05% by weight, relative to the total weight of the composition, and a step consisting in applying, to the treated skin, light radiation having a wavelength of between 360 and 450 nm, for at least 3 minutes.

25 Claims, No Drawings

METHOD FOR TREATING ACNE

The invention relates to a method for treating acneic skin using a composition comprising an anionic surfactant and exposure of the treated skin to light.

Sebum is normally an agent for moisturizing the epidermis.

It is the natural product of the sebaceous gland, which is an annex of the pilosebaceous unit. It is essentially a more or less complex mixture of lipids. Conventionally, the sebaceous gland produces squalene, triglycerides, aliphatic waxes, cholesterol waxes and, possibly, free cholesterol (Stewart, M. E., *Semin. Dermatol.* 11, 100-105 (1992)). The action of bacterial lipases converts a variable proportion of the triglycerides formed into free fatty acids.

The sebocyte constitutes the competent cell of the sebaceous gland. The production of sebum is associated with a programme of terminal differentiation of this cell. During this differentiation, the metabolic activity of the sebocyte is essentially directed towards the biosynthesis of lipids (lipogenesis) and more precisely towards fatty acid neosynthesis.

Hyperseborrhoeic greasy skin is characterized by an exaggerated secretion and excretion of sebum. Conventionally, a sebum level of greater than 200 µg/cm$^2$ measured on the forehead is considered as being characteristic of such greasy skin. Such skin is also often associated with a desquamation defect, a shiny complexion or a thick skin grain, which manifestations are perceived as being skin imperfections or aesthetic disorders.

Besides its unsightly appearance, it constitutes a breeding ground for the possible occurrence of complications. It affects the areas in which the sebaceous glands are numerous and results mainly from androgenic overstimulation of sebum production by these specific glands. Thus, hyperseborrhoea participates in the appearance of common acne lesions.

Common acne is a multi-factor disease that attacks skin rich in sebaceous glands (face, shoulder area, arms and intertriginous areas). It is one of the most common forms of dermatosis.

In its mildest form, this dermatosis affects almost all human beings. Its frequency is maximal at the age of puberty, but it may appear for the first time from the age of 7 to 9 and may extend beyond the age of 40. It also affects both men and women.

Among its commonest forms, mention may be made of comedonal acne, commonly referred to as juvenile acne, papulo-pustular and/or nodular acne, acne conglobata and "exogenous" acne appearing in reaction to inflammatory external factors. More specifically, acne is a disease of the sebaceous gland follicle. The following five pathogenic factors play a determining role in the constitution of acne: genetic predisposition, overproduction of sebum (seborrhoea), androgens, follicular keratinization disorders (comedogenesis), and bacterial colonization and inflammatory factors.

Specifically, in the deepest parts of the infundibular portion of the hair follicle, the formation of a larger than normal amount of keratinocytes is observed. These cells differentiate into horny cells which gradually obstruct the lumen of the follicular duct. The physiological process of continuous desquamation from the acroinfundibulum to the surface is disrupted by the increased adherence of the horny cells produced. A hyperkeratotic plug forms, which constitutes the comedone, the initial acne lesion. Finally, the local microorganism *Propionibacterium acnes* finds in the sebaceous follicle an ideal nutritive environment and is in particular responsible for seborrhoeic dermatitis and acne, in particular juvenile acne which more commonly affects adolescents.

The clinical "retention" manifestations observed may be of open or closed comedone type (microcysts, microcomedones or whiteheads). The inflammatory lesions derived from the retention lesions may be of the type such as papules, pustules, with indurated nodules, abscesses, fistulae or scar forms.

Thus, individuals with acne and acne-prone individuals have skin which is most commonly shiny with numerous imperfections on the face, inter alia (microcysts, microcomedones, whiteheads, papules, pustules, with indurated nodules, abscesses, fistulae or scar forms).

The other imperfections related to *Propionibacterium acnes* are, for example, rosacea, red patches, spots, papules, pustules, nodules, microcysts, and cysts.

Various compounds which, by topical application to the skin, are capable of reducing the proliferation of *P. acnes* have already been proposed for combating acne.

Unfortunately, the treatments currently available are not entirely satisfactory, in particular with regard to the side effects that are frequently associated therewith, such as irritant effects with certain topical agents such as retinoids and benzoyl peroxides. In addition, resistance of *P. acnes* to certain local antibacterial therapies is frequently observed.

There is therefore a need for a novel method for preventing and/or treating skin disorders related to *Propionibacterium acnes*, especially seborrhoeic dermatitis and in particular acne.

The applicant has demonstrated that, when carrying out a treatment method consisting in applying to acne-prone skin a composition comprising an anionic surfactant and in exposing the treated skin to light radiation, such a treatment method exhibits activity on the reduction or inhibition of microorganisms involved in the development of acne, and in particular *Propionibacterium acnes*.

A subject of the present invention is therefore a method for preventing and/or treating skin disorders related to *Propionibacterium acnes*, comprising:
  a step consisting in applying, to acneic skin, a dermatological composition comprising, in a physiologically acceptable medium, at least one anionic surfactant in an amount ranging from 0.001% to 0.05% by weight, relative to the total weight of the composition, and
  a step consisting in applying, to the treated skin, light radiation having a wavelength of between 360 and 450 nm, for at least 3 minutes.

The skin disorders related to *Propionibacterium acnes* and/or *Propionibacterium granulosum* are advantageously chosen from acne, in particular juvenile acne, seborrhoeic dermatitis, rosacea, red patches, spots, papules, pustules, nodules, microcysts and cysts.

Entirely preferably, the skin disorder related to *Propionibacterium acnes* is acne.

The term "physiologically acceptable medium" is intended to mean a medium compatible with keratin materials, which has a pleasant colour, odour and feel and which does not cause any unacceptable discomfort (stinging, tautness or red patches) liable to discourage the consumer from using it.

The term "keratin materials" is intended to mean the skin (body, face, area around the eyes, scalp), hair, eyelashes, eyebrows, body hair, nails and lips.

One of the steps of the method according to the invention consists in applying, to the skin, a dermatological composition comprising, in a physiologically acceptable medium, at least one anionic surfactant.

The anionic surfactant can be chosen from, alone or as mixtures, salts, in particular alkali metal salts such as sodium salts, ammonium salts, amine salts, amino alcohol salts or alkaline-earth metal salts, for example magnesium salts, of the following compounds:
  alkyl sulfates, alkyl ether sulfates, alkylamido ether sulfates, alkylarylpolyether sulfates, monoglyceride sulfates;
  alkylsulfonates, alkylamidesulfonates, alkylarylsulfonates, alpha-olefin sulfonates, paraffin sulfonates, alkyl phosphates;
  alkyl sulfosuccinates, alkylether sulfosuccinates, alkylamide sulfosuccinates, alkyl sulfoacetates;
  N-acylsarcosinates, N-acylglutamates;
  alkyl carboxylates;
  the alkyl and acyl groups of all these compounds containing from 6 to 24 carbon atoms and the aryl group preferably denoting a phenyl or benzyl group.

Mention may also be made of esters of $C_6$-$C_{24}$ alkyl and of polyglycoside-carboxylic acids, such as alkyl glucoside citrates, polyalkyl glycoside tartrates and polyalkyl glycoside sulfosuccinates; alkyl sulfosuccinamates, acyl isethionates and N-acyltaurates, the alkyl or acyl group of all these compounds containing from 12 to 20 carbon atoms.

Mention may also be made of the salts of acyl lactylates in which the acyl group contains from 8 to 20 carbon atoms.

Mention may also be made of alkyl-D-galactosideuronic acids and salts thereof, and also polyoxyalkylenated ($C_6$-$C_{24}$)alkyl ethercarboxylic acids, polyoxyalkylenated ($C_6$-$C_{24}$)alkyl($C_6$-$C_{24}$)aryl ether carboxylic acids and polyoxyalkylenated ($C_6$-$C_{24}$)alkylamido ether carboxylic acids and salts thereof, in particular those comprising from 2 to 50 ethylene oxide groups, and mixtures thereof.

As examples of alkyl sulfate salts, mention may be made of sodium, magnesium or ammonium salts of alkyl sulfates, and in particular sodium lauryl sulfate and ammonium lauryl sulfate.

As examples of alkyl ether sulfate salts, mention may be made of the sodium, magnesium or ammonium salts of alkyl ether sulfates, and in particular sodium lauryl ether sulfate, preferably comprising 2 or 3 mol of ethylene oxide (EO), and sodium myreth sulfate.

As examples of alkylsulfonate salts or alkylarylsulfonate salts, mention may be made of the sodium, ammonium or magnesium salts of alkylsulfonates or of alkylarylsulfonates, in particular of docusates, such as dioctyl sodium sulfosuccinate, or of alkylbenzenesulfonates.

As examples of alkyl phosphate salts, mention may be made of sodium, magnesium or ammonium salts of alkyl phosphates, and in particular of alkylaryl ether phosphates or of alkyl ether phosphates, preferably comprising 2 or 3 mol of EO.

As examples of alkyl carboxylate salts, mention may be made, in particular, of sodium, magnesium or ammonium salts of alkyl carboxylates, and in particular sodium stearate, sodium lauroyl sarcosinate and sodium lauroyl glutamate.

Preferably, the anionic surfactant is chosen from the alkyl sulfate salts, the acyl glutamate salts and the acyl lactylate salts as previously described, and a mixture thereof.

According to one preferred embodiment, the anionic surfactant is chosen from the acyl glutamate salts and the acyl lactylate salts as previously described, and a mixture thereof.

Preferentially, the anionic surfactant is chosen from sodium lauryl sulfate, sodium lauroyl glutamate and sodium lauroyl lactylate, and a mixture thereof.

According to one preferred embodiment, the anionic surfactant is chosen from sodium lauroyl glutamate and sodium lauroyl lactylate, and a mixture thereof.

The anionic surfactant, or mixture of anionic surfactants, is preferably present in the composition in an amount ranging from 0.001% to 0.04% by weight, relative to the total weight of the composition, preferably ranging from 0.0015% to 0.03% by weight, preferentially ranging from 0.0015% to 0.02% by weight and even better still ranging from 0.02% to 0.01% by weight.

The composition comprising a small amount of anionic surfactant observes the barrier function of the treated skin without irritating it.

The composition according to the invention, comprising the anionic surfactant or the mixture of anionic surfactants, can be provided in any formulation form conventionally used for topical application and in particular in the form of aqueous gels or of aqueous or aqueous/alcoholic solutions. It can also, by addition of a fatty or oily phase, be provided in the form of a dispersion of the lotion type, of an emulsion with a liquid or semi-liquid consistency of the milk type, obtained by dispersion of a fatty phase in an aqueous phase (O/W) or vice versa (W/O), or of a suspension or emulsion with a soft, semi-solid or solid consistency of the cream or gel type, or alternatively of a multiple emulsion (W/O/W or O/W/O), of a microemulsion, of a vesicular dispersion of ionic and/or non-ionic type, or of a wax/aqueous phase dispersion, or even of an anhydrous composition, or alternatively of a solid composition. These compositions will be prepared by those skilled in the art according to the usual methods.

They may also comprise, in the physiologically acceptable medium, the ingredients generally used in products of this type and well known to those skilled in the art, such as water, waxes, oils, gelling agents, thickeners, film-forming polymers, fillers, colorants, preservatives or fragrances, and a mixture thereof.

According to this step of the method, it is possible to apply 0.01 mg to 200 mg of dermatological composition comprising the surfactant, alone or as a mixture, in particular 0.02 mg to 100 mg of composition, per $cm^2$ of skin.

The method according to the invention also comprises a step consisting in applying, to the skin to be treated, light radiation having a wavelength of between 360 and 450 nm.

It is possible to perform this step consisting in applying light radiation before, after or at the same time as (simultaneously with) the step consisting in applying the dermatological composition comprising at least one surfactant. Preferably, the two steps take place simultaneously or, preferentially, the dermatological composition comprising at least one surfactant is applied to the skin in a first step, and then light radiation is applied to the skin in a second step.

It is possible to carry out a step of rinsing the skin, for example with water, between each step of the method.

It is also possible to leave on the composition comprising the surfactant, before carrying out the step of applying the light radiation and/or of rinsing.

Preferably, the light radiation used in the method according to the invention has a wavelength of between 400 and 450 nm.

The light radiation preferably has a fluence (amount of energy per unit surface area) ranging from 3 to 100/$cm^2$, and preferably ranging from 3 to 10 $J/cm^2$.

The light radiation may be a continuous or non-continuous light.

As a source of light radiation, mention may be made of arc lamps, such as xenon lamps and mercury lamps; fluorescent lamps; incandescent lamps such as halogens; LEDs and lasers. Filters, which filter out radiation with a wavelength of less than 360 nm or greater than 450 nm, can also be used with these lamps.

Mention may in particular be made of goLITE BLU from the company Philips, the Energylight HF 3319/01 lamp from the company Philips, the Dayvia White and Messa lamps from the company Solvital, the Lumino Plus lamp from the company Lanaform, the medibeam lamp from the company Medibeam, the M-LED 01 lamp from the company Meimed, the Lifemax light pod lamp from the company Lifemax, the Lite-Pad lamp from the company Reicorp, and the Camag Box 3 (4×8 W) lamp from the company Camag.

The duration of exposure to the light radiation of the treated skin is at least 3 minutes. Preferably, this duration of exposure can range from 3 to 30 minutes, in particular between 3 and 15 minutes and even better still between 3 and 10 minutes, whatever the order of the steps (one before the other or simultaneous).

By way of example, in the case of simultaneous application of the light radiation and of the composition comprising the anionic surfactant, the duration of exposure to the light can advantageously be between 3 minutes and 10 minutes. It is possible to perform rinsing of the composition, but this is not obligatory.

By way of example, in the case of application of the composition comprising the anionic surfactant and then application of the light radiation, the duration of exposure to the light can advantageously be between 3 minutes and 10 minutes. It is possible to leave on the composition comprising the surfactant for a period of from 1 second to 1 hour, before carrying out the step of applying the light radiation. It is possible to perform rinsing of the composition, before or after the step of applying the light radiation, but this is not obligatory.

EXAMPLES

Microbial suspensions of *P. acnes* (*P. acnes* ATCC 6919) were prepared by centrifugation, at 7000 g, of a 5-day culture at 35° C. of 100 ml of trypcase soy broth. The pellets obtained were resuspended in sterile physiological saline so as to obtain a level of $10^7$ CFU/ml (colony-forming units/ml).

The *P. acnes* suspensions were deposited on an Episkin® J13 reconstructed epidermis (1.1 cm$^2$) and left to adhere for 2 h at 37° C. After the 2 hours of adhesion, the epidermises were rinsed with sterile water in order to remove the bacteria which had not adhered. Next, the epidermises were treated with 25 microliters of an aqueous solution of anionic surfactant according to the concentrations and doses applied, described hereinafter:

| | Concentration of the aqueous solution of surfactant applied (% by weight) | Dose of surfactant applied to the epidermidis |
|---|---|---|
| Sodium lauroyl glutamate STEPAN ® SLL-FB from Stepan | 0.0075% (0.075 mg/ml) | 1.70 micrograms/cm$^2$ |
| Sodium lauroyl lactylate AMISOFT LS 11 from Ajinomoto | 0.0025% (0.025 mg/ml) | 0.57 micrograms/cm$^2$ |

The cultivatable viable bacteria were then counted on suitable culture media.

The booster effect of the light with the surfactants tested was evaluated: the number of bacteria on an epidermis treated with the tested surfactant but not irradiated was compared with the number of bacteria on an epidermis treated under the same conditions and exposed to light.

The light source used is a xenon lamp (reference OMNI300 from the company Lot-Oriel) coupled to a computer and a monochromator. This equipment makes it possible to select a wavelength and to irradiate a surface by means of a light guide. The guide is at a distance of 1.3 cm from the reconstructed skin. The powers of the light measured at the surface of the epidermis are described below:

| | Wavelength | | |
|---|---|---|---|
| | 405 nm | 430 nm | 600 nm |
| Power at the surface of the epidermis (in mW/cm$^2$) | 18.7 | 18.3 | 14.9 |

The irradiation time is 5 minutes. The doses received at the surface of the epidermis are the following:

| Wavelength | Dose of irradiation received at the surface of the skin (mJ/cm$^2$) |
|---|---|
| 405 nm | 5610 |
| 430 nm | 5490 |
| 600 nm | 4470 |

The following results were obtained:

| | Irradiation wavelength | *P. acnes* + surfactant without irradiation (in Log) | *P. acnes* + surfactant + irradiation (in Log) | Difference (in Log) |
|---|---|---|---|---|
| Sodium lauroyl glutamate | 405 nm | 4.47 | 3.65 | −0.82 |
| Sodium lauroyl glutamate | 430 nm | 4.47 | 3.85 | −0.62 |
| Sodium lauroyl glutamate | 600 nm | 4.47 | 4.22 | −0.25 |
| Sodium lauroyl lactylate | 405 nm | 5.08 | 4.02 | −1.06 |
| Sodium lauroyl lactylate | 430 nm | 5.08 | 4.08 | −1 |
| Sodium lauroyl lactylate | 600 nm | 4.85 | 4.46 | −0.39 |

In order to be significant, the difference between the number of bacteria on an epidermis treated with a surfactant but not irradiated and the number of bacteria on an epidermis treated under the same conditions and irradiated must be less than −0.5 log.

The results obtained show that skin treated with sodium lauroyl lactylate and sodium lauroyl glutamate and irradiated with radiation at the wavelengths of 405 nm and 430 nm exhibits a notable decrease in the number of bacteria. On the other hand, irradiation with radiation having a wavelength of 600 nm proves to be ineffective.

The invention claimed is:

1. A method for preventing and/or treating skin disorders related to *Propionibacterium acnes*, comprising:
   a step consisting in applying, to acneic skin, a dermatological composition comprising, in a physiologically acceptable medium, at least one anionic surfactant in an amount ranging from 0.001% to 0.05% by weight, relative to the total weight of the composition, and
   a step consisting in applying, to the acneic skin, light radiation having a wavelength of between 360 and 430 nm, for at between 3 and 30 minutes, and
   wherein the light radiation is from a source selected from the group consisting of an arc lamp; a fluorescent lamp; and incandescent lamp; a LED and a laser.

2. The method according to claim 1, in which the skin disorders related to *Propionibacterium acnes* are selected from the group consisting of acne, seborrhoeic dermatitis, rosacea, red patches, spots, papules, pustules, nodules, microcysts and cysts.

3. The method according to claim 2, in which the skin disorder related to *Propionibacterium acnes* is acne.

4. The method according to claim 2, in which the anionic surfactant is selected from the group consisting of alkyl sulfate salts in which the alkyl group contains from 6 to 24 carbon atoms, acyl glutamate salts in which the acyl group contains from 6 to 24 carbon atoms and acyl lactylate salts in which the acyl group contains from 8 to 20 carbon atoms, and a mixture thereof.

5. The method according to claim 2, in which the anionic surfactant is selected from the group consisting of sodium lauryl sulfate, sodium lauroyl glutamate and sodium lauroyl lactylate, and a mixture thereof.

6. The method according to claim 1, in which the skin disorder related to *Propionibacterium acnes* is acne.

7. The method according to 6, in which the anionic surfactant is selected from the group consisting of:
   salts of the following components:
      alkyl sulfates, alkyl ether sulfates, alkylamido ether sulfates, alkylarylpolyether sulfates, monoglyceride sulfates;
      alkylsulfonates, alkylamidesulfonates, alkylarylsulfonates, alpha-olefin sulfonates, paraffin sulfonates;
      alkyl phosphates;
      alkyl sulfosuccinates, alkylether sulfosuccinates, alkylamide sulfosuccinates, alkyl sulfoacetates;
      N-acylsarcosinates, N-acylglutamates;
      alkyl carboxylates;
   the alkyl and acyl groups of all these compounds containing from 6 to 24 carbon atoms and the aryl group preferably denoting a phenyl or benzyl group;
      esters of $C_6$-$C_{24}$ alkyl and of polyglycoside-carboxylic acids, such as alkyl glucoside citrates, polyalkyl glycoside tartrates and polyalkyl glycoside sulfosuccinates; alkyl sulfosuccinamates, acyl isethionates and N-acyltaurates, the alkyl or acyl group of all these compounds containing from 12 to 20 carbon atoms;
   acyl lactylates in which the acyl group contains from 8 to 20 carbon atoms;
   alkyl-D-galactoside uronic acids and salts thereof, and also polyoxyalkylenated ($C_6$-$C_{24}$)alkyl ethercarboxylic acids, polyoxyalkylenated ($C_6$-$C_{24}$)alkyl($C_6$-$C_{24}$)aryl ether carboxylic acids and polyoxyalkylenated ($C_6$-$C_{24}$)alkylamido ether carboxylic acids and salts thereof, and mixtures thereof.

8. The method according to claim 7, in which the anionic surfactant is selected from the group consisting of the alkyl sulfate salts in which the alkyl group contains from 6 to 24 carbon atoms, the acyl glutamate salts in which the acyl group contains from 6 to 24 carbon atoms and the acyl lactylate salts in which the acyl group contains from 8 to 20 carbon atoms, and a mixture thereof.

9. The method according to claim 6, in which the anionic surfactant is selected from the group consisting of alkyl sulfate salts in which the alkyl group contains from 6 to 24 carbon atoms, acyl glutamate salts in which the acyl group contains from 6 to 24 carbon atoms and acyl lactylate salts in which the acyl group contains from 8 to 20 carbon atoms, and a mixture thereof.

10. The method according to claim 6, in which the anionic surfactant is a salt selected from the group consisting of sodium, magnesium or ammonium salts.

11. The method according to claim 1, in which the anionic surfactant is selected from the group consisting of alkyl sulfate salts in which the alkyl group contains from 6 to 24 carbon atoms, the acyl glutamate salts in which the acyl group contains from 6 to 24 carbon atoms and the acyl lactylate salts in which the acyl group contains from 8 to 20 carbon atoms, and a mixture thereof.

12. The method according to claim 11, in which the salts are selected from the group consisting of sodium, magnesium or ammonium salts.

13. The method according to claim 1, in which the anionic surfactant is selected from the group consisting of sodium lauryl sulfate, sodium lauroyl glutamate and sodium lauroyl lactylate, and a mixture thereof.

14. The method according to claim 1, in which the anionic surfactant, alone or as a mixture, is present in the composition in an amount ranging from 0.002% to 0.01% by weight, relative to the total weight of the composition.

15. The method according to claim 1, in which the step consisting in applying light radiation is carried out after or at the same time as (simultaneously with) the step consisting in applying the dermatological composition comprising the anionic surfactant.

16. The method according to claim 1, in which the light radiation has at least one of the following characteristics:
   the light radiation has a fluence (amount of energy per unit surface area) of between 3 and 100 $J/cm^2$; and/or
   the light radiation is a continuous or non-continuous light.

17. The method according to claim 1, in which the duration of exposure to the light radiation is between 3 and 30 minutes, whatever the order of the steps (one before the other or simultaneous).

18. The method according to claim 1, in which the duration of exposure to the light radiation is between 3 and 15 minutes, whatever the order of the steps (one before the other or simultaneous).

19. The method according to claim 1, in which the duration of exposure to the light radiation is between 3 and 10 minutes, whatever the order of the steps (one before the other or simultaneous).

20. The method according to claim 1, in which the anionic surfactant is selected from the group consisting of alkyl sulfate salts in which the alkyl group contains from 6 to 24 carbon atoms, acyl glutamate salts in which the acyl group contains from 6 to 24 carbon atoms and acyl lactylate salts in which the acyl group contains from 8 to 20 carbon atoms, and a mixture thereof; and the anionic surfactant, alone or as a mixture, is present in the composition in an amount ranging from 0.002% to 0.01% by weight, relative to the total weight of the composition.

21. The method according to claim 20, in which the anionic surfactant is selected from the group consisting of sodium lauryl sulfate, sodium lauroyl glutamate and sodium lauroyl lactylate, and a mixture thereof.

22. The method according to claim 20, in which the anionic surfactant is selected from the group consisting of sodium lauroyl glutamate and sodium lauroyl lactylate, and a mixture thereof.

23. The method according to claim 1, in which the anionic surfactant is selected from the group consisting of sodium lauroyl glutamate and sodium lauroyl lactylate, and a mixture thereof.

24. The method according to claim 1, in which the light radiation has a fluence (amount of energy per unit surface area) of between 3 and 10 $J/cm^2$.

25. The method according to claim 1, wherein the light radiation is from a xenon lamp.

* * * * *